United States Patent [19]

Neiss et al.

[11] 4,364,940

[45] Dec. 21, 1982

[54] COMPOSITIONS FOR TREATING ACNE

[75] Inventors: Edward S. Neiss, New Canaan, Conn.; Bernard Loev, Scarsdale, N.Y.

[73] Assignee: USV Pharmaceutical Corporation, Tarrytown, N.Y.

[21] Appl. No.: 237,234

[22] Filed: Feb. 23, 1981

[51] Int. Cl.$^3$ ............................................. A61K 31/60
[52] U.S. Cl. .................................... 424/230; 424/338
[58] Field of Search ........................ 424/230, 232, 338

[56] References Cited

U.S. PATENT DOCUMENTS

| | | | |
|---|---|---|---|
| 3,535,422 | 10/1970 | Cox et al. | 424/164 |
| 4,126,681 | 11/1978 | Reller | 424/234 |
| 4,244,948 | 1/1981 | Boghosian et al. | 424/230 |

OTHER PUBLICATIONS

Chemical Abstracts 75:75899g, (1971).

*Primary Examiner*—Leonard Schenkman

[57] ABSTRACT

A composition for the treatment of acne in the form of a solution, lotion or cream containing from about 1 to 10% by weight of a compound of the formula

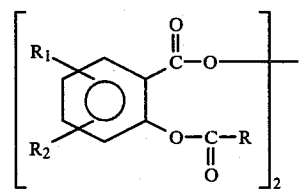

wherein R is an alkyl having up to 6 carbon atoms or aryl having up to 10 carbon atoms and $R_1$ and $R_2$ are independently hydrogen, lower alkyl having up to 6 carbon atoms, phenyl, phenyl-lower alkyl, lower alkylphenyl, halogen, halophenyl, trifluoromethyl, trifluoromethylphenyl, lower alkoxy, methylenedioxy, and lower alkoxyphenyl.

2 Claims, No Drawings

COMPOSITIONS FOR TREATING ACNE

The present invention relates to pharmaceutical compositions. It particularly relates to pharmaceutical compositions for the treatment of acne.

Salicylic acid has been reported to have comedolytic activity making it useful in the treatment of acne. (*J. Investigative Dermatology* 73, 434 (1979). The use of aspirin (acetylsalicyclic acid) and other salicylates in topical preparations for the treatment of acne has been suggested in U.S. Pat. No. 4,126,881; British Pat. No. 842,404; British Pat. No. 1,292,503; Canadian Pat. No. 938,555; French Pat. No. 2,077,798; and Japanese Pat. No. 73/03364. The effectiveness of the salicylates is probably due to their keratolytic, exfoliating and/or corneolytic activities.

Benzoyl peroxide compositions for the treatment of acne have been reported in U.S. Pat. No. 3,535,422. Benzoyl peroxide is probably useful because of its activity in inhibiting the growth *P. acne.*

A composition containing both benzoyl peroxide and salicylic acid for the treatment of acne has been reported in German Offenlegungsschrift No. 2 418 386.

Acetylsalicyloyl peroxides are known compounds and have been described in Pharm. Zeiting 47, 847 (1902).

It has now been found that acyl-salicyloyl peroxides of the formula

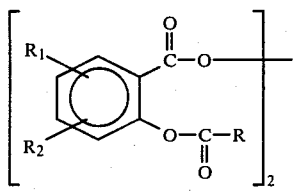

wherein R is an alkyl having up to 6 carbon atoms or aryl having up to 10 carbon atoms and $R_1$ and $R_2$ are independently hydrogen, lower alkyl having up to 6 carbon atoms, phenyl, phenyl lower alkyl, lower alkylphenyl, halogen, halophenyl, trifluoromethyl, trifluoromethylphenyl, lower alkoxy, methylenedioxy, and lower alkoxyphenyl are useful compounds in the treatment of acne, possessing both the desirable effects of the salicylates and benzoyl peroxide plus potent anti-bacterial activity.

The compounds are preferably applied to the acne-affected area of the skin in a vehicle in the form of a solution, cream or lotion. The composition contains about 1 to about 10% by weight of the active peroxide. Any solvent, lotion or cream suitable for application to the skin may be used as the vehicle.

The invention will be more fully illustrated in the examples which follow. These examples are given by way of illustration and are not to be considered as limiting.

EXAMPLE 1

O-Acetylsalicyloyl Peroxide

O-Acetylsalicyloyl chloride (12 g) was dissolved in ice-cold acetone (20 ml), and then 30% hydrogen peroxide (3.4 g) and anhydrous sodium sulfate (3 g) were added to the solution. To the reaction mixture was then added sodium bicarbonate (5.1 g) in portions over a period of 1 hr at 0°. The reaction mixture was stirred for an additional hour.

After filtration, a small amount of methanol was added to the filtrate and white needles precipitated upon standing. Filtration gave 1.8 g of product, m.p. 105°–106°.

EXAMPLE 2

A. Preparation of Lotion Vehicle

|  | % W/W |
|---|---|
| PHASE I |  |
| Promulgen D (Polyethylene glycol ether complexes of high molecular weight naturally occurring fatty alcohols) | 2.5 |
| Schercomol D1D (Diisopropyl dimerate) | 1.5 |
| Polyethylene Glycol 400 | 5.0 |
| Distilled Water | 88.2 |
| PHASE II |  |
| Avicel CL-611 (Microcrystalline cellulose) | 2.8 |

MANUFACTURING PROCEDURE

1. All of the materials in Phase I were mixed together in a suitable stainless steel container using a propeller type mixer, and heated to 75° C.
2. Phase II (Avicel CL-611) was quickly added to Phase I while mixing at high sheer. After 5 minutes high sheer agitation at 60° C., slow cooling was begun with moderate agitation to allow escape of entrapped air. The lotion was cooled to 30° C.
3. Q.S. for water loss.

B. Preparation of Product Containing Active Ingredient 7.4 g of the compound prepared according to Example 1 was triturated into 30 g of the lotion prepared according to Example 2A, using a mortar and pestle to effect thorough grinding and mixing. Additional lotion was then added with thorough mixing to bring the final concentration of the O-acetylsalicoyl peroxide to about 7.4% by weight.

EXAMPLE 3

Following the procedure of Example 2, a lotion containing about 1.48% by weight of O-acetylsalicyloyl peroxide was prepared.

The lotion of Example 3 was used on a moderate acne condition of the cheeks, forehead and skin. The lotion was applied twice daily (AM and PM) over 30 sec., and allowed to remain on both day and night. This treatment was continued over a 4 week period. A 75% reduction in the number of comedones was noted. In addition, a 90% reduction in the number of inflammatory papules was achieved in about 10 to 18 days.

The compositions of the present invention should be useful in the treatment of pruritic scaling dermatitis, infected scaly dermatitis, rosacea and other similar dermatites.

We claim:

1. A composition for the topical treatment of acne in the form of a lotion or cream containing from about 1 to 10% by weight of a compound of the formula

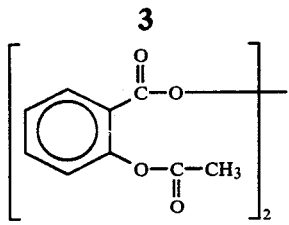
2. A process for treating acne which comprises applying to the acne-affected area of the skin an effective amount of a composition according to claim 1.
* * * * *